(12) United States Patent
Schuman et al.

(10) Patent No.: US 8,679,065 B2
(45) Date of Patent: Mar. 25, 2014

(54) APPARATUS FOR SUPPORTING MEDICAL LINES

(75) Inventors: Richard Schuman, Lake Oswego, OR (US); Earl Schuman, Lake Oswego, OR (US); Joseph Edward Okies, Portland, OR (US); Kathryn V. Schach, Beaverton, OR (US); Edward Harber, Portland, OR (US); Nathan Demarest, Portland, OR (US); Samuel E. Bowman, Portland, OR (US); Adriana Lyn Focke, Portland, OR (US)

(73) Assignee: Innovative Design Solutions Medical, LLC, Lake Oswego, OR (US)

( * ) Notice: Subject to any disclaimer, the term of this patent is extended or adjusted under 35 U.S.C. 154(b) by 0 days.

(21) Appl. No.: 13/305,627

(22) Filed: Nov. 28, 2011

(65) Prior Publication Data

US 2013/0138044 A1    May 30, 2013

(51) Int. Cl.
*A61M 5/32*  (2006.01)
*A47B 97/04*  (2006.01)
*A47F 1/04*  (2006.01)

(52) U.S. Cl.
USPC ........... 604/174; 604/177; 248/459; 211/60.1

(58) Field of Classification Search
USPC ............... 604/174, 177–180; 128/DIG. 26; 248/49, 68.1, 74.2, 74.3, 451, 459; 211/85.13, 60.1, 85.4, 89.01, 106, 211/181.1, 119
See application file for complete search history.

(56) References Cited

U.S. PATENT DOCUMENTS

| | | | | |
|---|---|---|---|---|
| 615,702 | A | * | 12/1898 | Hills .............................. 206/486 |
| 3,263,820 | A | * | 8/1966 | McFadden et al. .......... 211/60.1 |
| 4,113,222 | A | | 9/1978 | Frinzel |
| 4,181,220 | A | * | 1/1980 | Zicko ......................... 206/315.2 |
| 4,432,468 | A | | 2/1984 | Siff et al. |
| 4,511,158 | A | | 4/1985 | Varga et al. |
| 4,606,735 | A | * | 8/1986 | Wilder et al. ................. 604/180 |
| 4,639,980 | A | | 2/1987 | Peterson |
| 4,654,026 | A | | 3/1987 | Underwood |
| 4,690,674 | A | | 9/1987 | Daglish |
| 4,795,429 | A | * | 1/1989 | Feldstein ......................... 604/80 |
| 4,844,397 | A | | 7/1989 | Skakoon et al. |
| 4,865,583 | A | | 9/1989 | Tu |
| 4,896,820 | A | * | 1/1990 | Harrington ................... 229/100 |
| 4,928,712 | A | | 5/1990 | Mele |
| 4,970,900 | A | | 11/1990 | Shepherd et al. |
| 4,988,062 | A | | 1/1991 | London |
| 4,999,885 | A | | 3/1991 | Lee |
| 5,224,674 | A | | 7/1993 | Simons |
| 5,265,822 | A | | 11/1993 | Shober, Jr. et al. |
| 5,328,487 | A | | 7/1994 | Starchevich |

(Continued)

*Primary Examiner* — Quynh-Nhu H Vu
(74) *Attorney, Agent, or Firm* — Klarquist Sparkman, LLP

(57) ABSTRACT

An exemplary line holder comprises a sheet having creases that extend between opposing sides and define a plurality of panels. The creases are foldable in alternating opposite directions such that the sheet is foldable along the creases between an open configuration and a pleated configuration. The line holder further comprises aligned groups of holes that are arranged along a direction substantially transverse to the creases, with each aligned group of holes comprising one hole in each of the panels. The line holder further comprises slots, each connecting a pair of the holes and intersecting one of the creases. When the sheet is in the pleated configuration, each aligned group of holes forms a corridor through the panels, and the slots are aligned to form pathways extending from the intersected creases to the corridors, such that medical lines can be inserted into the corridors.

15 Claims, 6 Drawing Sheets

(56) References Cited

U.S. PATENT DOCUMENTS

| | | | |
|---|---|---|---|
| 5,334,186 A | 8/1994 | Alexander | |
| 5,367,127 A * | 11/1994 | Dormon | 174/146 |
| 5,876,371 A | 3/1999 | Yokoyama et al. | |
| 5,924,658 A | 7/1999 | Shiery et al. | |
| 5,971,168 A * | 10/1999 | Proulx | 211/85.4 |
| 6,065,490 A | 5/2000 | Falcone, Jr. | |
| 6,079,678 A | 6/2000 | Schott et al. | |
| 6,273,278 B1 * | 8/2001 | Enyedy et al. | 211/85.4 |
| 6,290,192 B1 | 9/2001 | Messerli | |
| 6,375,017 B1 | 4/2002 | Schattner et al. | |
| 6,382,568 B1 | 5/2002 | Snell | |
| 6,721,977 B2 | 4/2004 | Solesbee et al. | |
| D503,231 S | 3/2005 | Daugherty | |
| 6,930,244 B1 * | 8/2005 | Nebel | 174/486 |
| 7,052,158 B2 | 5/2006 | Rodriquez et al. | |
| 7,083,150 B2 | 8/2006 | Newkirk et al. | |
| 7,098,406 B1 | 8/2006 | Hammonds | |
| 7,457,506 B1 | 11/2008 | Osborne, II | |
| 7,766,289 B2 | 8/2010 | Newkirk et al. | |
| D628,416 S | 12/2010 | Heimbrock et al. | |
| 7,874,410 B2 | 1/2011 | Fulbrook et al. | |
| 2001/0017340 A1 | 8/2001 | Cernosek et al. | |
| 2001/0049504 A1 | 12/2001 | Gautsche et al. | |
| 2004/0118982 A1 | 6/2004 | Shillings et al. | |
| 2005/0006534 A1 | 1/2005 | Shillings | |
| 2005/0103948 A1 * | 5/2005 | Vu et al. | 248/65 |
| 2005/0103949 A1 | 5/2005 | Ross et al. | |
| 2006/0020257 A1 | 1/2006 | Mambourg | |
| 2006/0113432 A1 | 6/2006 | Driskell | |
| 2006/0237597 A1 | 10/2006 | D'Andria | |
| 2007/0078401 A1 | 4/2007 | Servoss | |
| 2007/0259555 A1 | 11/2007 | Conforti | |
| 2008/0011907 A1 | 1/2008 | Jacobsma | |
| 2009/0019678 A1 | 1/2009 | Taylor | |
| 2010/0010475 A1 * | 1/2010 | Teirstein et al. | 604/528 |

* cited by examiner

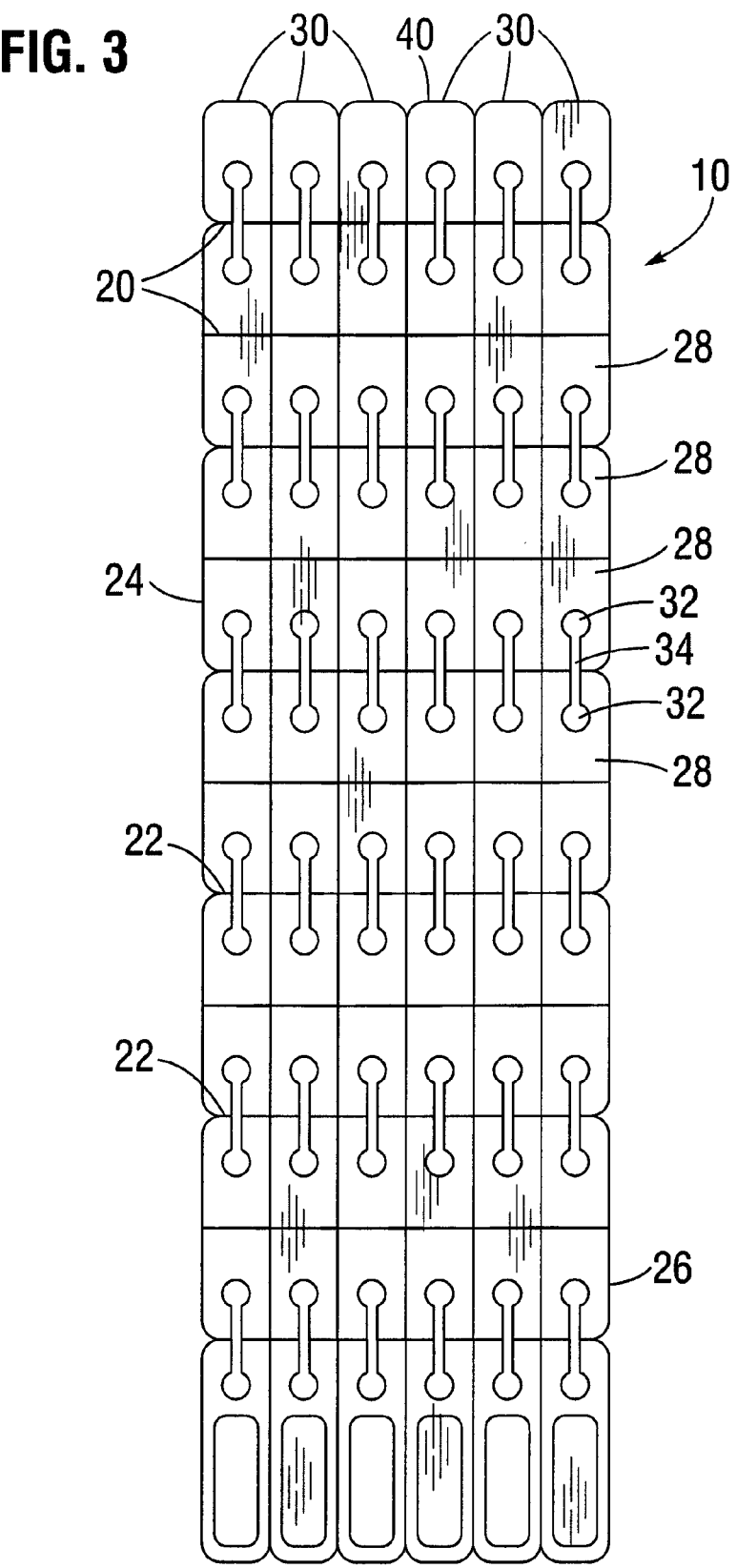

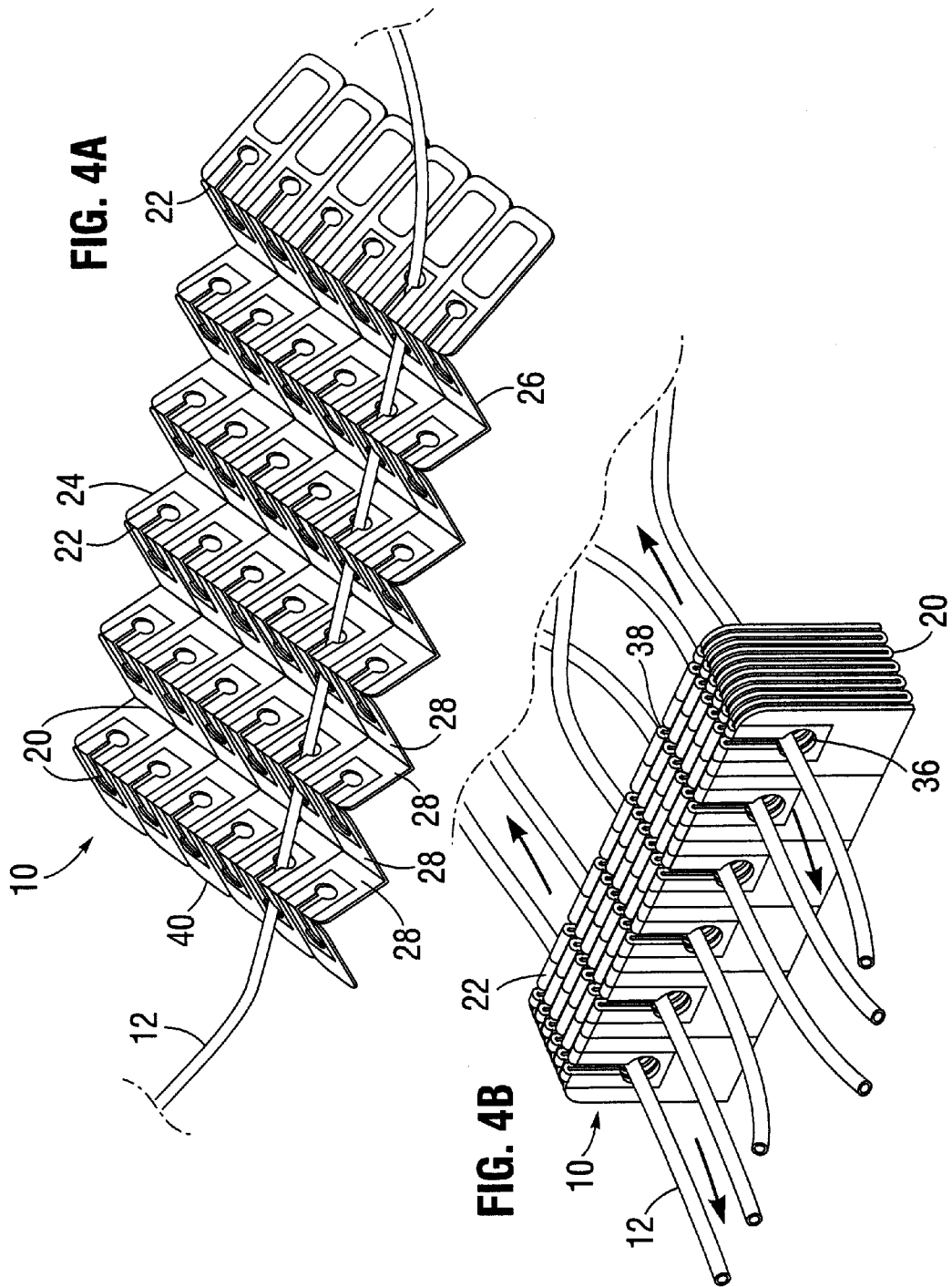

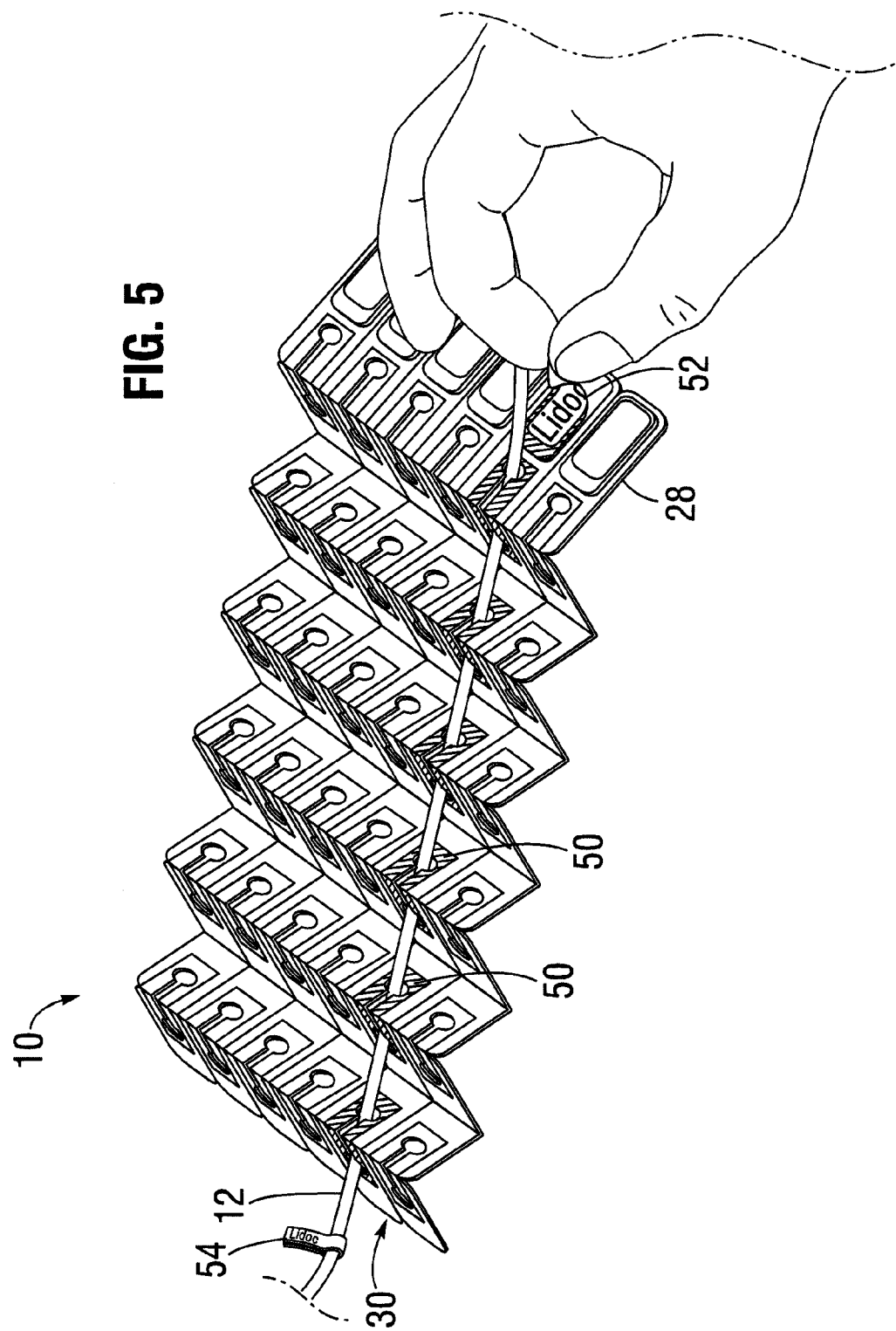

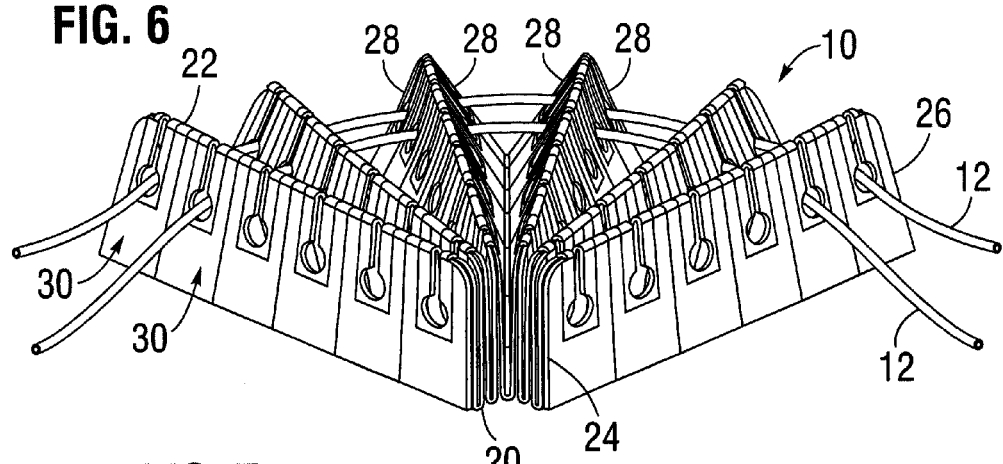
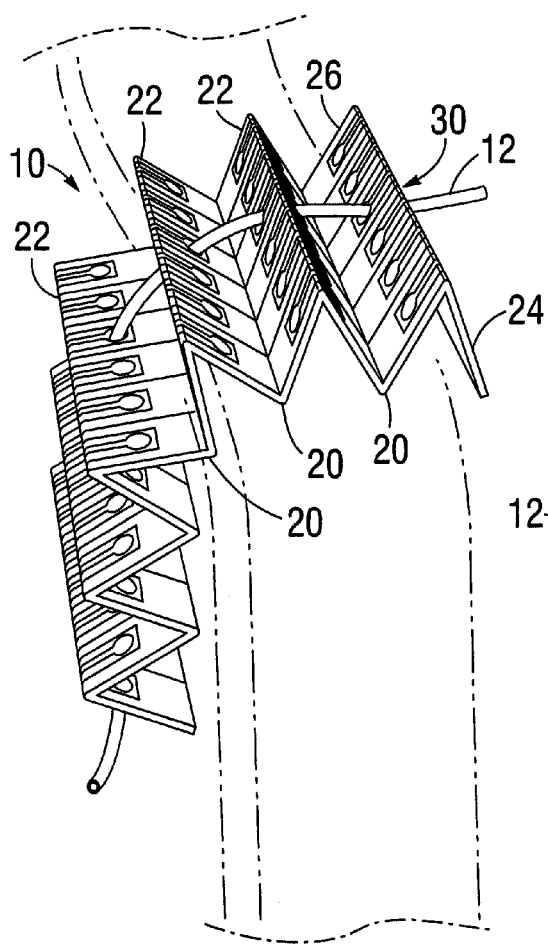
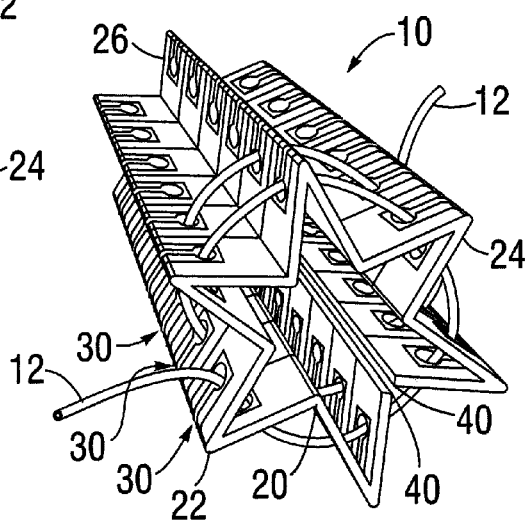

APPARATUS FOR SUPPORTING MEDICAL LINES

FIELD

The present disclosure relates to an apparatus for use with medical lines for patients.

BACKGROUND

In various healthcare settings, patients lying on a bed often have several medical lines attached to their body for various purposes, such as IV drips, electrical monitors, catheters, etc. Management of these medical lines has historically been difficult and time intensive for healthcare professionals. In recent years, the number of these medical lines used per patient has increased, especially with certain populations of critically ill patients. However, no effective solution for addressing this problem has been developed.

The medical lines often get tangled, twisted, knotted, etc. as the patient moves around, the sources of the lines move around, lines are disconnected and reconnected, and new lines are added. This often results in a tangled, disorganized "rat's nest" of lines adjacent to the patient. FIG. 1 shows a mild example of this, though much more tangled, disorganized rat's nests often occur.

This problem presents major and complex challenges for healthcare professionals, such as patient safety, establishment and maintenance of line order, patient mobility, patient transfers, system mobility, physical interferences, time utilization, and visual distress.

The propensity for line tangling increases as the number of lines increases. Many lines include multiple injection ports. Many of the IV tubings connect into the same central line, which with any movement or transfer of the patient creates and expands the chaotic jumble of tubings. Patients coming from the operating room very often have multiple lines that have become tangled in part due to the movement from the operating table to the bed. This also applies to critically ill patient transports to intra-hospital departments such as imaging services (CT, MRI), angiography, and other inter-hospital transfers via helicopter or ambulance.

This all creates an extreme burden on the healthcare team, especially RNs, for providing a constant environment of safety. In many cases, such as upon a return of a patient from the OR to the ICU, such as with post cardiac surgery patients, it is typical for nurses to spend 30-60 minutes in identifying, checking, and detangling lines. It is critical for nurses to be able to have the constant knowledge of which medications are running through which lines, etc. Further, each shift of nurses must be able to validate the individual medication drips, injection ports, tubings, pressure lines, transducers, etc. It is standard for patient safety to be able to follow each line from start to finish—from patient to pump, bag, monitor, etc. Ultimately, this requires additional commitment of time each shift to detangle, validate, and recreate an environment of order, albeit temporary.

In addition, critically ill patients are often turned in bed every two hours and lines easily tangle with turning. Some patients will still have multiple lines, but have improved enough to be able to sit on the edge of the bed or up in a chair at bedside. this movement of the patient can easily create actual and visual disarray and disorder of the lines, despite attempts by nurses to maintain order.

Furthermore, families of patients experience a burden of stress and anxiety having their loved ones in a critical care unit. The visual disarray of the "rat's nest" of medical lines can cause added anxiety, distress and concern for the families regarding confidence in the safety and effectiveness of the care being provided to their loved one.

SUMMARY

Described herein are embodiments of an apparatus for holding and organizing medical lines for a patient. In some embodiments, a line holder comprises a sheet of material having a plurality of creases in the sheet of material that extend between two opposing side edges of the sheet of material and define a plurality of sheet panels separated by the creases. The creases are foldable in alternating opposite directions such that the sheet of material is capable of being folded along the creases between an open configuration and a pleated configuration. The line holder further comprises a plurality of aligned groups of holes in the sheet of material that are arranged along a direction substantially transverse to the creases, with each aligned group of holes comprising one hole in each of the panels. When the sheet of material is in the pleated configuration, each aligned group of holes forms a corridor through the plurality of panels. The line holder further comprises a plurality of slots in the sheet of material, each connecting a pair of the holes of one of the aligned group of holes and intersecting one of the creases between the pair of holes. When the sheet of material is in the pleated configuration, the slots are aligned to form pathways extending from the intersected creases to the corridors, such that the pathways are configured to allow medical lines to be inserted into the corridors.

In some embodiments, when the line holder resiliently expands from the pleated configuration with a medical line inserted into a corridor, the line holder locks the medical line into the corridor.

In some embodiments, the line holder further comprises removable indicators coupled to the sheet of material, each of the removable indicators comprising indicia corresponding to a respective one of the aligned groups of holes. The removable indicators can comprise peel-off tabs that are color coded with tracks in the line holder and can be written upon.

In some embodiments, the line holder can be configured to be curved or arched, so as to route medical lines around a corner or over an obstacle, or to take up excess line length.

Some embodiments of the line holder comprise multiple tracks, with the tracks being coupled to respective medical lines at three or more intermediate points located between an origin and a patient attachment point. Each intermediate point corresponds to a different opening in the line holder, and the medical lines are held substantially parallel to one another between the intermediate points.

Exemplary methods disclosed herein comprise: compressing a line organizer into a pleated configuration; resiliently deforming aligned slots in the line organizer; inserting medical lines through the deformed aligned slots and into a series of substantially parallel tracks in the line organizer; and expanding the line organizer from the pleated configuration to an expanded configuration to lock the medical lines within the tracks of the line organizer at three or more spaced apart locations.

In some of these methods, the tracks comprise a series of openings connected in pairs by the slots, and compressing the line organizer into the pleated configuration comprises folding a sheet of material in alternating opposite directions along a series of parallel creases to position the series of openings in a substantially coaxial alignment.

In some methods, resiliently deforming the aligned slots comprises bending opposing portions of the line organizer adjacent to the aligned slots in opposite directions to increase the width of the aligned slots.

In some methods, expanding the line organizer to the expanded configuration comprises releasing compressive pressure on the line organizer and allowing the line organizer to resiliently unfold along the creases.

Some of these methods further comprise: removing a tab from the line organizer, the tab comprising indicia correlating the tab with one of the tracks; and attaching the tab to the medical line that is positioned in the track indicated by the tab, the tab being attached to the medical line at a location spaced from the line organizer.

The foregoing and other objects, features, and advantages of the invention will become more apparent from the following detailed description, which proceeds with reference to the accompanying figures.

BRIEF DESCRIPTION OF THE DRAWINGS

FIG. 3 is a plan view of an exemplary line holder in a flattened configuration.

FIG. 4A is a perspective view of the line holder of FIG. 3 in an open configuration with a medical line engaged with the line holder.

FIG. 4B is a perspective view of the line holder of FIG. 3 in a pleated configuration with several medical lines engaged with the line holder.

FIG. 5 is a perspective view of the line holder of FIG. 3 in an open configuration with a medical line engaged with the line holder, showing a peel-off tab corresponding to the engaged medical line.

FIGS. 6-8 show exemplary line holders in curved or arched configurations and engaged with medical lines.

DETAILED DESCRIPTION

In this disclosure, the terms "a", "an" and "at least one" encompass one or more of the specified elements. That is, if two of a particular element are present, one of these elements is also present and thus "an" element is present. The phrase "and/or" means "and", "or" and both "and" and "or". Further, the term "coupled" generally means electrically, electromagnetically, and/or physically (e.g., mechanically or chemically) coupled or linked and does not exclude the presence of intermediate elements between the coupled or associated items absent specific contrary language. Unless specifically stated otherwise, processes and methods described herein can be performed in any order and in any combination, including with other processes and/or method acts not specifically described. The exemplary embodiments disclosed herein are only preferred examples of the invention and should not be taken as limiting the scope of the invention.

Figure 2:
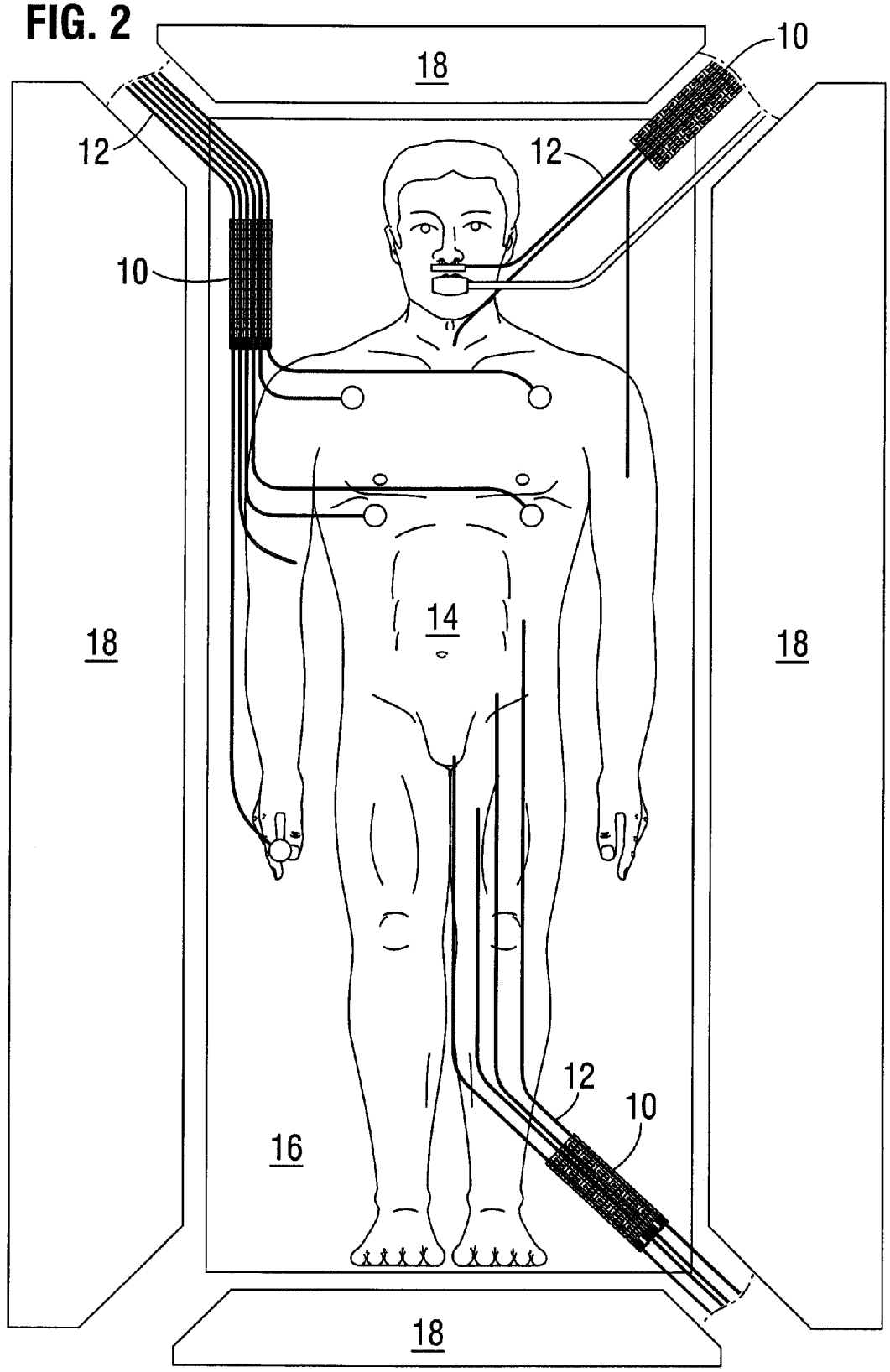
FIG. 2 shows a patient having multiple medical lines attached to his body, the lines being organized with exemplary line holders.

Described herein are embodiments of a line holder 10 for organizing medical lines. One embodiment of a line holder 10 is shown in FIGS. 2 and 3. As shown in FIG. 2, one or more line holders 10 can be used to organize medical lines 12 attached to a patient 14. The medical lines 12 can comprise a variety of different types of lines, such as tubes, wires, cords, catheters, etc., each having different diameters, materials, flexibilities, colors, transparencies, lengths, and purposes. The terms "lines" and "medical lines" are to be construed broadly and include a wide array of lines used across various healthcare fields, including medical, dental, veterinary, and related fields.

Figure 1:
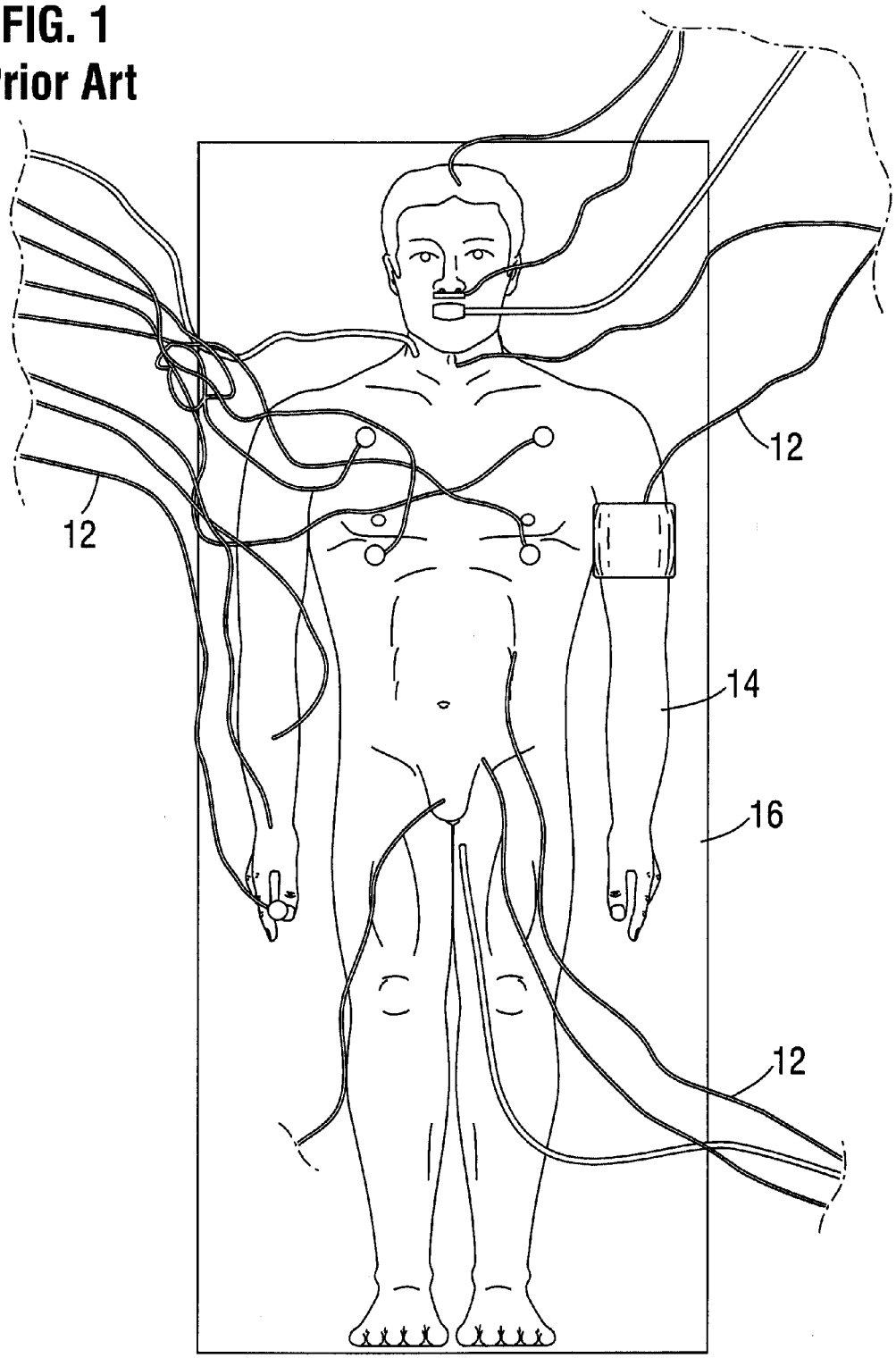
FIG. 1 shows a patient having multiple medical lines attached to his body, the lines being disorganized.

In FIG. 2, the patient 14 is lying on a bed 16 and three holders 10 are utilized to organize the medical lines 12 into three groups of lines, each routed from the patient over a different corner of the bed 16. In comparison to the "rat's nest" of FIG. 1, the lines 12 are much more organized and confined in FIG. 2. Routing the lines 12 over the corners of the bed 16 can also allow the work areas 18 at the sides of the bed to remain clear. FIG. 2 represents just an example of how the line holder 10 can be used to organize and manage medical lines 12, as any number of line holders can be used in any desirable configuration. For example, two or more line holders 10 can be used along the same line 12 or group of lines. Further, each line holder 10 can be of any length.

Use of the line holders 10 to organize medical lines can simplify and expedite identification of lines and the task of following each line from end to end, as well as increase safety and confidence. Although the line holder 10 is shown in use with a patient lying on a bed in FIG. 2, the line holder 10 can be used in various other healthcare settings, such as with a patient sitting, standing or walking, in an ambulance or helicopter, and/or on a gurney or a backboard. Furthermore, the line holder 10 can be used in various healthcare settings, such as medicine, dentistry, etc.

Additional advantages and benefits of utilizing the line holder 10 can include avoiding putting the wrong drug in the wrong line, identifying air bubbles in the lines, creating a more visually pleasing appearance for patients and their family, reducing workload and stress for healthcare providers, providing increased access to the patient, reducing the load on the patient caused by the weight of the lines, improving hygiene, increasing the mobility of the patient and the system, reducing the time and complexity of adding and removing lines, increasing the stability of pumps and bags attached to the lines, reducing the chance of lines pulling out of the patient, and avoiding kinks and knots in the lines. Furthermore, the line holder 10 can be lightweight, waterproof, cheap and disposable, and aesthetically pleasing. The line holder 10 can be laminated (multi-layered), coated with drugs or other chemicals, sticky, skid-free, and can comprise a variety of other materials. In addition, as shown in FIG. 4A, segments of the medical lines 12 that are engaged with the line holder 10 are visible along the length of the line holder such that each line can be more easily traced across the line holder, especially if the line holder is particularly long.

As shown in FIGS. 2-4, the line holder 10 comprises a thin, foldable sheet of material with a plurality of openings for engaging medical lines 12. The sheet comprises a plurality of creases 20 extending between two opposing side edges 24, 26. In some embodiments, the sheet can comprise at least two creases, at least three creases, at least four creases, and/or at least five creases. The creases 20 define a plurality of sheet panels 28 that are separated by the creases. In some embodiments, the line holder can comprise at least three, at least four, at least five, and/or at least six panels 28. The creases 20 are foldable in alternating opposite directions such that the sheet is capable of being folded along the creases 20 between an open configuration and a pleated configuration. The pleated configuration is defined as substantially the configuration shown in FIG. 4B, with the panels 28 being compressed together side-by-side in "accordion pleats" or slightly spaced apart from a fully pleated state. The open configuration is defined as an expanded configuration ranging from being expanded slightly from the pleated configuration shown in FIG. 4B to being fully expanded to a substantially flat configuration shown in FIG. 3. FIG. 4A shows an example of an intermediate open configuration of the line holder when engaged with medical lines 12.

In the illustrated embodiments, the creases 20 are spaced apart at equal intervals along the length of the line holder (when laid flat as in FIG. 3) such that the panels 28 between the creases 20 are of equal length. In other embodiments, the creases 20 can be spaced apart at non-equal intervals along the length of the line holder such that the panels 28 are not all the same size. In such embodiments, when the line holder is in the pleated configuration, some of the panels 28 can have different heights and can protrude above the other panels. For example, one pair of panels on either end of the line holder and one pair of intermediate panels can be taller than the other panels, such that the three panel pairs extend above the others. In such an embodiment, medical lines 12 can be supported by only those three raised panel pairs, and can be positioned above the other panels. Further, some medical lines can be supported by only the three raised panel pairs, while other medical lines can run through all the panels at a lower level.

As shown in FIG. 3, the line holder 10 further comprises a plurality of tracks 30, each comprising an aligned group of holes 32 for engaging medical lines 12. The line holder 10 can comprise any number of tracks 30, such as at least two, at least three, at least four, at least five, at least six, at least seven, and/or at least eight tracks 30. The tracks 30 can be arranged substantially parallel to one another along a length of the line holder 10. Each track 30 preferably includes one hole 32 in each of the panels 28. The holes 32 can be arranged in pairs, with each pair of holes being in two adjacent panels 28. In some embodiments, not all of the holes are paired with another hole in the track 30. For example, the line holder can have a single hole 32 in one or both end panels 28 that is not paired with another hole 32.

The line holder 10 further comprises a plurality of slots 34. The slots 34 can have a substantial width forming openings in the sheet of material, or the slots 34 can comprise mere slits in the sheet of material such that material edges on opposite sides of the slots are touching or nearly touching each other. Each slot 34 connects a pair of the holes 32 in one of the tracks 30. Each slot 34 extends between a pair of holes 32 and intersects one of the creases 20. Every other crease 20 can be a crease that is intersected by slots 34, and such creases are herein termed intersected creases 22. Each slot 34 and respective single hole 32 or pair of holes 32 can form a contiguous opening, or engagement portion, that has a narrower width along the slot 34 and greater width at the hole(s) 32. Each track 30 can comprise at least two or at least three of these engagement portions.

When the line holder 10 is in the pleated configuration, as shown in FIG. 4B, each aligned group of holes 32 in each track 30 forms a corridor 36 through the panels. In some embodiments, the aligned holes 32 can be coaxial and/or the corridors 36 can be cylindrical when the line holder is in the pleated configuration. Further, in the pleated configuration, the slots 34 are substantially aligned to form open pathways 38 extending from the intersected creases 22 to the corridors 36. The pathways 38 are configured to allow medical lines 12 to be inserted through the pathways and into the corridors 36.

In some embodiments, the sheet of material can comprise elastically resilient and/or elastically deformable material, such as a polymeric material. In some of these embodiments, the line holder 10 can intrinsically expand to a substantially flattened, open configuration when no medical lines 12 are engaged and the line holder is free from outside compressive forces. In these embodiments, the line holder 10 can be compressed to the pleated configuration in order to insert medical lines 12 into the corridors 36 of each track 30, and then the line holder can be freed from compressive force and allowed to resiliently expand back toward the flattened configuration.

In other embodiments, the sheet of material can plastically deform to some extent when folded about the creases 20, such that manual force is used to expand the line holder from the pleated configuration.

In either case, due to the presence of the medical lines 12 in the holes 32, the line holder 10 can only expand to a partially open configuration short of the flattened configuration. As the line holder 10 expands, the panels 28 pivot from a substantially parallel, side-by-side orientation, as shown in FIG. 4B, to an oblique orientation, as shown in FIG. 4A. While the panels pivot, the holes 32 also pivot, causing the effective height of the holes 32 (i.e., the dimension of the holes perpendicular to the axial direction of the medical lines 12) to decrease. When the effective height of a hole 32 is about equal to the diameter of the medical line, the medical line 12 physically impedes further pivoting of the panel 28, inhibiting the expansion of the line holder 10. This physical contact between the holes 32 and the lines 12 can create frictional resistance in the axial direction of the lines, thus inhibiting the lines 12 from sliding axially along the tracks. Furthermore, different tracks 30 in the line holder 10 can comprise different sized holes 32, in order to accommodate different diameter medical lines 12. The holes 32 can be circular, ovular, elliptical, etc., and can have a smooth, brushed, serrated, or other margin configuration to allow variation in line mobility.

In order to insert a medical line 12 through the pathways 38 and into the corridors 36 when the line holder is in the pleated configuration, the pathways 38 can be configured to temporarily expand in width to at least the diameter of the respective medical line 12. In the pleated configuration, the panels 28 are arranged side-by-side, such that all the panels can be bent or deformed in the same way at the same time. Once the medical line enters the corridor 36, the pathway 38 can return to its natural, smaller width to retain the medical line within the holes 32. To facilitate this process, the material adjacent to the pathways 38 can be at least partially elastic. In one exemplary process, a person can grip the two opposing sides of a given pathway 38 and bend them apart in opposite directions to widen the pathway, then insert a medical line 12 into the corridor 36, then release the two opposing sides to resiliently close back together. In another exemplary process, a person can forcibly press a medical line 12 against the slots 34 of a pathway 38 to force the pathway to widen and allow the medical line to slide through the pathway and into the corridor 36. Medical lines 12 can be removed from the line holder 10 when the line holder is in the pleated configuration in the same ways the medical lines can be inserted.

When the line holder is in an expanded configuration, the panels no longer are arranged side-by-side as they are in the pleated configuration. Instead, each panel is oriented at an angle relative to its adjacent panels. Because the panels are no longer oriented substantially parallel and side-by-side, they can no longer be bent or deformed as easily. In particular, in the open configuration the slots 34 are more resistant to separating apart to allow entry and removal of medical lines 12 from the holes 32. The medical lines 12 thus become mechanically locked into the holes 32 when the line holder expands to an open configuration. In some embodiments, the line holder 10 can lock a medical line at least three, at least four, or at least six spaced apart locations along a length of the line. The medical lines also become physically gripped by the rotation of the holes 32, resisting axial sliding of the lines relative to the line holder.

In some embodiments, based on the rigidity of the sheet material and the shape of the holes 32 and slots 34, the lines 12 can be forcibly pulled out of the line holder even when the line holder is in the open locked configuration. For example, in a situation where a patient yanks on a medical line with a strong force, the line holder 10 can be configured to release the medical line 12 to reduce the chance that the line is pulled out of or off of the patient. This can also prevent transfer of the yanking force to other lines engaged by the line holder. In other embodiments, the line holder can be more rigid, such as made of metal or with narrower slots 34, such that the lines 12 are more securely locked into place when the line holder is in the open locked configuration.

The material and thickness of the line holder can be selected such that it has a desired rigidity. The line holder is preferably not too flimsy like tissue paper, as it needs to withstand a hospital environment and repeated handling and it needs to be robust enough to hold medical lines in place. The line holder is also preferably not so rigid that is unbendable without application of considerable force, as might be the case with relatively thick metal material. Preferably, the line holder is sturdy and robust, yet resilient enough to support medical lines without substantially flattening or releasing and to flex to allow insertion of lines in the slots.

The line holder 10 can be repeatedly compressed and expanded, such as to repeatedly insert and remove medical lines 12. For example, the line holder 10 can be compressed to the pleated configuration a first time in order to insert one or more medical lines, then expanded to the open configuration to lock in the lines and hold them in substantially parallel tracks at spaced apart contact points along each track. The line holder 10 can then be compressed back to the pleated configuration in order to remove one or more of the lines 12, add one or more additional lines, and/or move one or more of the lines from one track 30 to another track. The line holder 10 can then be re-expanded to the open configuration to lock the lines, and the process can be repeated any number of times. Thus, the line holder 10 is adapted to repeatedly reorganize the lines 12 as the patient moves and/or the lines need to be replaced, realigned, untangled, etc.

The line holder 10 can be waterproof or impervious to liquids, such as water and blood, so that the line holder maintains its integrity in various medical environments. The line holder can be comprised of a material that is inherently impervious to fluids, such as a polymeric or metallic material, or the line holder can be impregnated, laminated, and/or coated with a material to make it impervious to liquids. The line holder 10 can further comprise a variety of other materials to serve purposes other than liquid resistance. For example, the line holder can be coated with drugs or other substances. In one embodiment, the line holder can be coated with antimicrobial agents, such as metal or alloy-based agents (e.g., silver-, copper-, or zinc-based compounds), antimicrobial peptides, antibiotics (e.g., minocycline or nitrofurazone), and/or chemical compounds.

Because the line holder 10 can comprise a thin sheet of material, it can be very lightweight, cheaply manufactured, and/or disposable. For example, the line holder 10 can comprise a sheet of polymeric material that is die-cut to impart the creases 28, holes 32 and slots 34, and optionally printed as desired. Such an embodiment can weigh only a few grams and can cost only a few pennies to manufacture. Due to the light weight, the line holder 10 does not weigh down the medical lines 12 and can "float" in space along with the lines rather than needing to rest on a surface. In other embodiments, the line holder 10 can be configured to rest on a surface. The light weight of the line holder 10 can further reduce pulling forces on the lines 12 and therefore be less likely to pull a line out of the patient and/or create discomfort for the patient. In other embodiments, the line holder 12 can comprises heavier material and/or include weights in order to create a "paper weight" type line holder that anchors the medical lines at a surface, such as at a corner of the bed 16. In some embodiments, the line holder can be configured to be coupled, such as releasably attached, to a surface to anchor the lines 12.

The line holder 10 can be a disposable product, such that one line holder is used for only one patient and/or more than one line holder can be used for the same patient in a disposable manner. The line holder 10 can further be recyclable. In some embodiments, the line holder can be more robust and configured to be cleaned and reused. For example, some embodiments can be reused for multiple patients and/or more than once for the same patient.

In some embodiments, the line holder 10 can comprise color coded tracks 30 such that each of the tracks 30 has a different color. The color coded tracks 30 can be continuous or dashed. Each track 30 can comprise plurality of color portions that have the same color. For example, each of the rectangular portions 50 of the track 30 in FIG. 5 can have the same color. In some embodiments, other indicators can be used to distinguish each track 30 from one another, such as patterns or symbols. In these embodiments, each particular track 30, with its unique identifying color, pattern, symbol, etc., can correspond to a particular type of medical line, or a particular feature of that track. For example, a red track can be designed for use with a specific red medical line, or a red track can indicate that the holes 32 of that track are of a particular size or shape.

In some embodiments, the line holder 10 can comprise one or more removable indicators coupled to the sheet of material, with each of the removable indicators comprising indicia corresponding to a respective one of the tracks 30. For example, as shown in FIG. 5, the removable indicators 52 can comprise peel-off tabs that are marked with colors and/or symbols that identify the type of medical line 12 engaged in the track 30. The indicators 52 can also be written on. In the example shown, the peel-off tabs 52 are marked with "Lidocaine" to indicate that the medical line 12 in track 30 is for conducting lidocaine to the patient. The peel-off tab 52 in FIG. 5 further comprises a coloring or pattern that matches the coloring or pattern of the rectangular portions 50 of track 30. In the embodiment shown, the peel-off tab 52 is coupled to an end panel 28, while in other embodiments, removable indicators can be coupled to the sheet at other locations. Furthermore, in other embodiments, the removable indicators can comprise tear off portions of the sheet or portions of the line holder that are removably attachable to the sheet with any known releasably attachable mechanism.

In some embodiments, the removable indicators, such as the peel-off tabs 52, can be coupled to the corresponding medical line 12 at a location spaced apart from the line holder 10. For example, in the embodiment shown in FIG. 5, the peel-off tab 54 shown represents the tab 52 after it has been removed from the sheet and applied around the medical line 12. The tab 54 can be adhesively attachable, mechanically attachable, or otherwise attachable to the medical line 12. The tab 54 can be attached to the medical line 12 at a location adjacent to the patient 14 at an insertion point, or the tab 54 can be attached to the line 12 adjacent to a pump, bag, monitor or other end portion away from the patient. In some embodiments, the line holder 10 can comprise two or more removable indicators 52 for each track 30, such that one can be attached to the line 12 adjacent the patient and the other can be attached to the line at the opposite end. For example, one tab can be marked "upstream" while the other is marked "downstream", or the tabs can be marked "patient" and "pump", or other marking schemes can be used to differentiate the opposite ends of the lines 12. Marking the lines 12 with the removable indicators can simplify and speed the process of tracing a line from the patient, through the line holder, and to a pump, bag, etc., as well as help identify the purpose of the line.

FIGS. 6-8 show embodiments of the line holder 10 that are configured to route medical lines 12 in non-linear paths, such as to route the lines around corners, over obstacles, or to take up excess line length.

In some embodiments, such as FIG. 6, the line holder 10 can be foldable into a curved configuration with the panels 28 compressed together to a first extent on the first side 24 of the sheet and the panels compressed together to a lesser extent on the second side 26 of the sheet. By compressing one side of the line holder more than the opposite side, the tracks 30 form a curved path through the line holder. This enables the line holder to hold medical lines 12 in curved paths. Multiple lines 12 can be held in generally parallel, or concentric, curved paths through the line holder, as shown in FIG. 6. To keep the side 24 more compressed than the side 26, a clip or other mechanism can be attached to the side 24. In some embodiments, the creases 20 in the sheet of material can be preformed such that the line holder 10 naturally assumes a curved configuration similar to that shown in FIG. 7 when free of external compressive forces.

As shown in FIG. 7, the line holder 10 can also be configured to be curved or arched in other manners, such as curved about an axis that parallel to the creases 20. In the example shown in FIG. 7, the line holder is configured to route medical line 12 over or around an obstacle, such as a patient's arm or leg, the edge of a bed, or a bed side rail. In these embodiments, at least some of the intersected creases 22 are folded to a greater extent (i.e., a smaller included angle) that the non-intersected creases 20 on the bottom of the line holder. Further, in these embodiments, each of the creases 20, 22 can have a substantially consistent fold angle between the first and second sides 24, 26 of the sheet, and the creases can all be substantially parallel to another.

As shown in FIG. 8, some embodiments of the line holder 10 can be folded into a looped, or annular, configuration such that opposing ends 40 of each track 30 are brought together and the tracks form annular tracks. These embodiments can comprise stiffer material in order to maintain the annular shape without collapsing. In this configuration, excess length in medical lines 12 can be taken up by wrapping the lines around the line holder 10 one or more times. In these embodiments, medical lines 12 can enter and exit the line holder at any hole 32 of the tracks 30. Further, individual lines 12 can occupy multiple tracks 30 and can jump from one track to another track after each loop around the line holder 10 in order to take up excess length in the lines. Similar to the embodiment shown in FIG. 7, in these embodiments, at least some of the intersected creases 22 are folded to a greater extent (i.e., a smaller included angle) than the non-intersected creases 20 on the inside of the line holder 10. Further, in these embodiments, each of the creases 20, 22 can have a substantially consistent fold angle between the first and second sides 24, 26 of the sheet, and the creases can all be substantially parallel to one another.

In some embodiments, the line holder 10 can be sterilizable and/or and can be pre-packaged in a sterile condition.

The line holder 10 can be used with a variety of patient types and with a variety of medical procedures. Some common examples can include: critically ill patients, post-cardiac surgery patients, patients having had major abdominal surgeries, burn patients or patients with loss of skin, patients in the operating room prior to surgery, patients in the ICU, ER patients, and patients being transported between different facilities.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A line holder for organizing multiple elongate medical lines for a patient, the line holder comprising:
    a sheet of foldable material;
    a plurality of creases in the sheet of material, the creases extending between two opposing side edges of the sheet of material and defining a plurality of sheet panels separated by the creases, the creases being foldable in alternating opposite directions such that the sheet of material is capable of being folded along the creases between an open configuration in which the panels are spaced from one another and a compact pleated configuration in which the panels abut one another;
    a plurality of aligned groups of holes in the sheet of material, the aligned groups of holes being arranged along a direction substantially transverse to the creases, each aligned group of holes comprising one hole in each of the panels, wherein when the sheet of material is in the pleated configuration each aligned group of holes forms a corridor through the plurality of panels; and
    a plurality of slots in the sheet of material, each slot connecting a pair of the holes of one of the aligned group of holes and intersecting one of the creases between the pair of holes, wherein when the sheet of material is in the pleated configuration the slots are aligned to form pathways extending from the intersected creases to the corridors, the pathways being configured to allow medical lines to be inserted into the corridors, whereby the line holder is capable of being folded into a looped configuration such that the corridors form annular tracks.

2. The line holder of claim 1, wherein the sheet of material comprises a resiliently deformable material.

3. The line holder of claim 1, wherein when the sheet of material is in the pleated configuration, the pathways are configured to be resiliently deformed to allow entry of medical lines into the respective corridors.

4. The line holder of claim 2, wherein when the line holder resiliently expands from the pleated configuration with a medical line inserted into a corridor, the line holder locks the medical line into the corridor.

5. The line holder of claim 1, further comprising removable indicators coupled to the sheet of material, each of the removable indicators comprising indicia corresponding to a respective one of the aligned groups of holes.

6. The line holder of claim 5, wherein the removable indicators are color coded with the respective aligned groups of holes.

7. The line holder of claim 1, wherein the sheet of material comprises at least five creases and six panels, and each aligned group of holes comprises at least three pairs of holes.

8. The line holder of claim 1, wherein the plurality of aligned groups of holes comprises at least six aligned groups of holes.

9. The line holder of claim 1, wherein the sheet of material is impervious to liquids.

10. The line holder of claim 1, wherein the sheet of material is coated with a drug or an antimicrobial agent.

11. The line holder of claim 1, wherein the two opposing side edges of the sheet of material comprise a first side and a second side, and wherein the line holder is foldable into a curved configuration with the panels compressed together to a first extent on the first side of the sheet and with the panels compressed together to a lesser extent on the second side of the sheet.

12. The line holder of claim 1, wherein the line holder is foldable into an arched configuration with the intersected creases being folded to a greater extent that the other creases.

13. The line holder of claim 12, wherein the line holder is foldable into a loop, such that excess medical line length can be taken up by wrapping it around the line holder.

14. The line holder of claim 1, further comprising at least two medical lines inserted into the corridors, wherein the medical lines comprise both fluid lines and electrical lines.

15. A system for organizing medical lines for a patient, comprising:
   a plurality of medical lines, each having an origin end away from the patient and a connection point at the patient;
   a line holder comprising multiple tracks, each track coupled to a respective one of the medical lines at three or more intermediate points between the origin and the connection point, each intermediate point corresponding to a different opening in the line holder, such that the medical lines are held substantially parallel to one another between the intermediate points; and
   a plurality of tabs that are color-coded with respective tracks of the line holder, the tabs being removable from the line holder and attachable to the medical lines that are coupled to the tracks of the same color wherein the line holder is foldable to a pleated configuration for insertion and removal of the medical lines, and expandable to a locked configuration wherein each of the medical lines is mechanically held by the line holder at three or more spaced apart engagement portions of the line holder, each engagement portion comprising two openings connected by a slot that is narrower than the openings, whereby the line holder is capable of being folded into a looped configuration such that the tracks form annular tracks.

* * * * *